(12) United States Patent
Steiner et al.

(10) Patent No.: US 8,084,420 B2
(45) Date of Patent: *Dec. 27, 2011

(54) RAPID ACTING AND LONG ACTING INSULIN COMBINATION FORMULATIONS

(75) Inventors: Solomon S. Steiner, Mount Kisco, NY (US); Roderike Pohl, Sherman, CT (US)

(73) Assignee: Biodel Inc., Danbury, CT (US)

(*) Notice: Subject to any disclaimer, the term of this patent is extended or adjusted under 35 U.S.C. 154(b) by 189 days.

This patent is subject to a terminal disclaimer.

(21) Appl. No.: 12/324,717

(22) Filed: Nov. 26, 2008

(65) Prior Publication Data
US 2009/0137455 A1 May 28, 2009

Related U.S. Application Data

(63) Continuation-in-part of application No. 11/695,562, filed on Apr. 2, 2007, now Pat. No. 7,713,929, which is a continuation-in-part of application No. 11/537,335, filed on Sep. 29, 2006, now abandoned.

(60) Provisional application No. 60/990,814, filed on Nov. 28, 2007, provisional application No. 60/744,687, filed on Apr. 12, 2006, provisional application No. 60/721,698, filed on Sep. 29, 2005.

(51) Int. Cl.
*A61K 38/28* (2006.01)
*A61K 38/16* (2006.01)
*A61K 31/185* (2006.01)
*C07K 14/62* (2006.01)

(52) U.S. Cl. ............ 514/6.8; 514/6.9; 514/7.3; 530/300; 530/303; 530/324

(58) Field of Classification Search ................ None
See application file for complete search history.

(56) References Cited

U.S. PATENT DOCUMENTS

| | | |
|---|---|---|
| 2,143,590 A | 1/1939 | Scott |
| 2,626,228 A | 1/1953 | Petersen |
| 2,819,999 A | 1/1958 | Schlichtkrull |
| 3,649,456 A | 3/1972 | De Benneville et al. |
| 3,683,635 A | 8/1972 | Campanelli |
| 3,906,950 A | 9/1975 | Cocozza |
| 3,921,637 A | 11/1975 | Bennie et al. |
| 4,129,560 A | 12/1978 | Zoltobrocki |
| 4,153,689 A | 5/1979 | Hirai |
| 4,196,196 A | 4/1980 | Tiholiz |
| 4,211,769 A | 7/1980 | Okada |
| 4,272,398 A | 6/1981 | Jaffe |
| 4,294,829 A | 10/1981 | Suzuki |
| 4,343,898 A | 8/1982 | Markussen |
| 4,377,482 A | 3/1983 | Rivier |
| 4,459,226 A | 7/1984 | Grimes |
| 4,489,159 A | 12/1984 | Markussen |
| 4,511,505 A | 4/1985 | Morihara |
| 4,659,696 A | 4/1987 | Hirai |
| 4,861,627 A | 8/1989 | Mathiowitz |
| 4,866,051 A | 9/1989 | Hunt |
| 4,946,828 A | 8/1990 | Markussen |
| 5,006,343 A | 4/1991 | Benson |
| 5,042,975 A | 8/1991 | Chien |
| 5,145,684 A | 9/1992 | Liversidge et al. |
| 5,188,837 A | 2/1993 | Domb |
| 5,204,108 A | 4/1993 | Illum |
| 5,260,306 A | 11/1993 | Boardman et al. |
| 5,352,461 A | 10/1994 | Feldstein et al. |
| 5,354,562 A | 10/1994 | Platz |
| 5,364,838 A | 11/1994 | Rubsamen |
| 5,458,135 A | 10/1995 | Patton et al. |
| 5,474,978 A | 12/1995 | Bakaysa |
| 5,482,927 A | 1/1996 | Maniar |
| 5,484,606 A | 1/1996 | Dhabhar et al. |
| 5,492,112 A | 2/1996 | Mecikalski et al. |
| 5,503,852 A | 4/1996 | Steiner et al. |
| 5,514,646 A | 5/1996 | Chance et al. |
| 5,534,488 A | 7/1996 | Hoffmann |
| 5,547,929 A | 8/1996 | Anderson, Jr. et al. |
| 5,562,909 A | 10/1996 | Allcock et al. |

(Continued)

FOREIGN PATENT DOCUMENTS
CA  2 136 704  5/1995
(Continued)

OTHER PUBLICATIONS

Definition of derivative and analog from http://cancerweb.ncl.ac.uk/omd/about.html, pp. 1-5. Accessed Jul. 7, 2005.*
"Human Insulin", GenBank Accession No. AAA59172, pp. 1-2, accessed Feb. 17, 2009.
"Bovine Insulin", GenBank Accession No. ACD35246, pp. 1-2, accessed Feb. 17, 2009.
"Types of insulin", http://www.diabetes.org/for-parents-and-kids/diabetes-care/types-actions.jsp, pp. 1-2, accessed Feb. 17, 2009.
U.S. Appl. No. 12/348,839, filed Jan. 5, 2009, Kashyap, et al.
"FDA Approves Rapid-acting insulin ApidraB from treatment of children with diabetes", http://www.medicalnewstoday.com/articles/127409.php, pp. 1-6 (2008). Accessed Apr. 30, 2009.
Actrapid, "Summary of product characteristics", http://emc.medicines.org.uk/medicine/3513/SPC/Actrapid+100+IU+ml,+Solution+for+Injection+in+a+vial/, pp. 1-6; revised (2007); (accessed Apr. 20, 2009).
Insulin from Diabetes Forecast, *2008 Resource Guide*, RG11-RG14. (2008).

(Continued)

*Primary Examiner* — Julie Ha
(74) *Attorney, Agent, or Firm* — Pabst Patent Group LLP

(57) ABSTRACT

An injectable formulation containing a rapid acting insulin and a long acting insulin has been developed. The pH of the rapid acting insulin is adjusted so that the long acting insulin, remains soluble when they are mixed together. Preferably, the formulation is administered before breakfast, provides adequate bolus insulin levels to cover the meal and basal insulin for up to 24 hours, and does not produce hypoglycemia after the meal. Lunch and dinner can be covered by two bolus injections of a fast, rapid, or very rapid acting insulin. Alternatively, by adjusting the ratio of rapid to long acting insulin, the long acting insulin may be shortened to a 12 hour formulation, and re-administered to the patient at dinner time, providing a safe and effective basal insulin level until morning. As a result, a patient using intensive insulin therapy should only inject three times a day.

16 Claims, 7 Drawing Sheets

U.S. PATENT DOCUMENTS

| | | |
|---|---|---|
| 5,577,497 A | 11/1996 | Mecikalski et al. |
| 5,650,486 A | 7/1997 | Felippis |
| 5,653,961 A | 8/1997 | McNally et al. |
| 5,653,987 A | 8/1997 | Modi et al. |
| 5,658,878 A | 8/1997 | Bäckström et al. |
| 5,672,359 A | 9/1997 | Digenis |
| 5,693,338 A | 12/1997 | Milstein |
| 5,740,794 A | 4/1998 | Smith et al. |
| 5,747,445 A | 5/1998 | Bäckström et al. |
| 5,763,396 A | 6/1998 | Weiner et al. |
| RE35,862 E | 7/1998 | Steiner et al. |
| 5,785,049 A | 7/1998 | Smith et al. |
| 5,785,989 A | 7/1998 | Stanley et al. |
| 5,807,315 A | 9/1998 | Van Antwerp et al. |
| 5,849,322 A | 12/1998 | Ebert et al. |
| 5,874,064 A | 2/1999 | Edwards et al. |
| 5,877,174 A | 3/1999 | Ono et al. |
| 5,888,477 A | 3/1999 | Gonda et al. |
| 5,898,028 A | 4/1999 | Jensen |
| 5,901,703 A | 5/1999 | Ohki et al. |
| 5,912,011 A | 6/1999 | Makino et al. |
| 5,929,027 A | 7/1999 | Takama et al. |
| 5,952,008 A | 9/1999 | Bäckström et al. |
| 5,976,569 A | 11/1999 | Milstein |
| 5,985,309 A | 11/1999 | Edwards et al. |
| 5,997,848 A | 12/1999 | Patton et al. |
| 6,051,256 A | 4/2000 | Platz et al. |
| 6,063,910 A | 5/2000 | Debenedetti |
| 6,071,497 A | 6/2000 | Steiner et al. |
| 6,099,517 A | 8/2000 | Daugherty |
| 6,132,766 A | 10/2000 | Sankaram et al. |
| 6,153,613 A | 11/2000 | Ono et al. |
| RE37,053 E | 2/2001 | Hanes et al. |
| 6,248,363 B1 | 6/2001 | Patel et al. |
| 6,254,854 B1 | 7/2001 | Edwards et al. |
| 6,264,981 B1 | 7/2001 | Zhang |
| 6,294,204 B1 | 9/2001 | Rossling et al. |
| 6,310,038 B1 | 10/2001 | Havelund |
| 6,331,318 B1 | 12/2001 | Milstein |
| 6,395,744 B1 | 5/2002 | Adams et al. |
| 6,423,344 B1 | 7/2002 | Platz et al. |
| 6,428,771 B1 | 8/2002 | Steiner et al. |
| 6,432,383 B1 | 8/2002 | Modi |
| 6,436,443 B2 | 8/2002 | Edwards et al. |
| 6,440,463 B1 | 8/2002 | Feldstein et al. |
| 6,444,226 B1 | 9/2002 | Steiner et al. |
| 6,447,753 B2 | 9/2002 | Edwards et al. |
| 6,465,425 B1 | 10/2002 | Tracy |
| 6,503,480 B1 | 1/2003 | Edwards et al. |
| 6,518,239 B1 | 2/2003 | Kuo et al. |
| 6,582,728 B1 | 6/2003 | Platz |
| 6,592,904 B2 | 7/2003 | Platz et al. |
| 6,635,283 B2 | 10/2003 | Edwards et al. |
| 6,652,885 B2 | 11/2003 | Steiner et al. |
| 6,676,931 B2 | 1/2004 | Dugger |
| 6,685,967 B1 | 2/2004 | Patton |
| 6,737,045 B2 | 5/2004 | Patton |
| 6,949,258 B2 | 9/2005 | Zhang |
| 6,960,561 B2 | 11/2005 | Boderke |
| 7,030,084 B2 | 4/2006 | Ekwuribe et al. |
| 7,089,934 B2 | 8/2006 | Staniforth et al. |
| 7,192,919 B2 | 3/2007 | Tzannis |
| 7,279,457 B2 | 10/2007 | Pohl et al. |
| 2001/0039260 A1 | 11/2001 | Havelund |
| 2001/0043934 A1 | 11/2001 | L'Italien et al. |
| 2002/0198140 A1 | 12/2002 | Havelund |
| 2003/0017211 A1 | 1/2003 | Steiner |
| 2003/0064097 A1 | 4/2003 | Patel et al. |
| 2003/0068378 A1 | 4/2003 | Chen et al. |
| 2003/0172924 A1 | 9/2003 | Staniforth et al. |
| 2003/0194420 A1 | 10/2003 | Holl et al. |
| 2004/0096403 A1 | 5/2004 | Steiner |
| 2004/0151774 A1 | 8/2004 | Pauletti et al. |
| 2004/0157928 A1 | 8/2004 | Kim et al. |
| 2004/0077528 A1 | 9/2004 | Steiner |
| 2004/0182387 A1 | 9/2004 | Steiner |
| 2004/0247628 A1 | 12/2004 | Lintz et al. |
| 2005/0080000 A1 | 4/2005 | Thurow et al. |
| 2005/0153874 A1 | 7/2005 | Cheatham |
| 2005/0203001 A1 | 9/2005 | Arbit |
| 2005/0214251 A1 | 9/2005 | Pohl et al. |
| 2006/0067891 A1 | 3/2006 | Modi |
| 2007/0134279 A1 | 6/2007 | Stern |
| 2007/0155654 A1 | 7/2007 | Langkjaer |
| 2007/0086952 A1 | 9/2007 | Steiner |
| 2007/0235365 A1 | 10/2007 | Pohl et al. |
| 2008/0039365 A1 | 2/2008 | Steiner et al. |
| 2008/0039368 A1 | 2/2008 | Steiner et al. |
| 2008/0085298 A1 | 4/2008 | Pohl et al. |
| 2008/0090753 A1 | 4/2008 | Pohl et al. |
| 2008/0096800 A1 | 4/2008 | Pohl et al. |

FOREIGN PATENT DOCUMENTS

| | | |
|---|---|---|
| DE | 247684 | 7/1987 |
| EP | 0 069 715 | 1/1983 |
| EP | 0 122 036 | 10/1984 |
| EP | 0 220 958 | 5/1987 |
| EP | 0 237 507 | 9/1987 |
| EP | 0 257 915 | 2/1988 |
| EP | 0 360 340 | 3/1990 |
| EP | 0 364 235 | 4/1990 |
| EP | 0 606 486 | 12/1993 |
| EP | 0748213 | 12/1996 |
| EP | 1 114 644 | 7/2001 |
| EP | 1 428 524 | 6/2004 |
| EP | 96911738 | 6/2004 |
| GB | 2 069 502 | 8/1981 |
| GB | 2240337 | 7/1991 |
| JP | 2149545 | 2/1992 |
| JP | 63020301 | 1/1998 |
| WO | WO 90/13285 | 11/1990 |
| WO | WO 91/04011 | 4/1991 |
| WO | WO 91/08764 | 6/1991 |
| WO | WO 91/16882 | 11/1991 |
| WO | WO 92/04069 | 3/1992 |
| WO | WO 92/08509 | 5/1992 |
| WO | WO 93/02712 | 2/1993 |
| WO | WO 93/17728 | 9/1993 |
| WO | WO 93/18754 | 9/1993 |
| WO | WO 94/00291 | 1/1994 |
| WO | WO 95/00127 | 1/1995 |
| WO | WO 95/11666 | 5/1995 |
| WO | WO 95/31979 | 11/1995 |
| WO | WO 95/34294 | 12/1995 |
| WO | WO 96/10996 | 4/1996 |
| WO | WO 96/36314 | 11/1996 |
| WO | WO 96/36352 | 11/1996 |
| WO | WO 97/33531 | 9/1997 |
| WO | WO 97/49386 | 12/1997 |
| WO | WO 98/42367 | 10/1998 |
| WO | WO 98/42368 | 10/1998 |
| WO | WO 98/42749 | 10/1998 |
| WO | WO 99/52506 A1 | 10/1999 |
| WO | WO 01/00654 | 1/2001 |
| WO | WO 01/07107 | 2/2001 |
| WO | WO 02/11676 | 2/2002 |
| WO | WO 03/057170 | 7/2003 |
| WO | WO 03/086345 | 10/2003 |
| WO | WO 03/094951 | 11/2003 |
| WO | WO 03/101395 | 12/2003 |
| WO | WO 2004/056314 | 8/2004 |
| WO | WO 2004/075919 | 9/2004 |
| WO | WO 2004/080401 | 9/2004 |
| WO | WO 2005/089722 | 9/2005 |
| WO | WO 2006/088473 | 8/2006 |
| WO | WO 2007/041481 | 4/2007 |
| WO | WO 2007/047948 | 4/2007 |
| WO | WO 2007/121256 | 10/2007 |

OTHER PUBLICATIONS

Kashyap, "Design and evaluation of biodegradable, biosensitive in situ gelling system for pulsatile delivery of insulin" *Biomaterials*, 28(11):2051-60 (2007). Epub Jan. 19, 2007.

Lantus, "Lantus prescribing information-Aventis Pharmaceuticals", http://products.sanofi-aventis.us/lantus/lantus.html, pp. 1-45. Accessed Apr. 30, 2009.

Levemir from www.levemir.com, pp. 1-15 (2007). Accessed Apr. 30, 2009.

Talrose, et al., "Radiation resistivity of frozen insulin solutions and suspensions", *Int. J. Appl. Radiat. Isot.*, 32(10):753-6 (1981).

Traitel, et al., "Characterization of glucose-sensitive insulin release systems in simulated in vivo conditions", *Biomaterials*, 21(16):1679-87 (2000).

Velosulin, "Information for health professionals, Production Data Sheet", http://www.medsafe.gov.nz/profs/datasheet/v/VelosulinMCinj.htm, pp. 1-5; (2000); (accessed Apr. 20, 2009).

Zhang, et al., "Modulated insulin permeation across a glucose-sensitive polymeric composite membrane", *J. Control Release*, 80(1-3):169-78 (2002).

Aungst & Rogers, "Site dependence of absorption-promoting actions of laureth-9, Na salicylate, Na2EDTA, and aprotinin on rectal, nasal, and buccal insulin delivery", *Pharm. Res.*, 5(5):305-308 (1988).

Bauer, et al.,"Assessment of beta-adrenergic receptor blockade after isamoltane, a 5-HT1-receptor active compound, in healthy volunteers," *Clin. Pharmacol Ther* 53:76-83 (1993).

Benita, "Characterization of Drug-Loaded Poly(d,l-lactide) Microspheres," *J. Pharm. Sci.*,73: 1721-1724 (1984).

Berge, et al. "Pharmacuetical Salts," *J. Pharmaceutical Sciences* 66(1):1-19 (1997).

Brange, et al., Chemical stability of insulin 1: hydrolytic degradation during storage of pharmaceutical preparations, *Pharm. Res.*, 9:715-726 (1992).

Brange and Langkjoer, "Insulin structure and stability", *Pharm Biotechnol.*, 5:315-50 (1993).

Cefalu, et al, "Inhaled Human Insulin Treatment in Patients with type 2 diabetes mellitus," *Ann. Int. Med.*, 134: 203-7 (2001).

Cerasi, et al., "Decreased sensitivity of the pancreatic beta cells to glucose in prediabetic and diabetic subjects. A glucose dose-response study," *Diabetes* 21(4): 224-34 (1972).

Cheatham and Pfuetzner, "Desirable dynamics & performance of inhaled insulin compared to subcutaneous insulin given at mealtime in type 2 diabetes: A report from the technosphere/insulin study group" *Diabetes Technology & Therapeutics* 6:234-235 (2004).

Costello, et al., "Zinc inhibition of mitochondrial aconitase and its importance in citrate metabolism in prostate epithelial cells", *Journ. Biol. Chem.*, 272(46):28875-28881 (1997).

Davidson, et al., "Effect of premixed nph and regular insulin on glucose control and health-related quality of life in patients with type-2 diabetes mellitus", *Endocrine Practice*, 3(6):331-336 (1997).

De Sousa, et al., "Biocompatibility of EDTA, EGTA and citric acid", *Braz. Dent. J.*, 16:3-8 (2005).

Dieter Köhler, "Aerosols for Systemic Treatment", *Lung (Suppl)*, 677-684 (1990).

Dunn, "Zinc-ligand interactions modulate assembly and stability of the insulin hexamer", *Biometals*, 18(4):295-303 (2005).

Edelman, "Type II Diabetes Mellitus," *Advances in Internal Medicine*, 43:449-500 (1998) (Abstract).

Edelman, et al., "A double-blinded placebo-controlled trial assessing pramlintide treatment in the setting of intensive insulin therapy in type 1 diabetes", *Diabetes Care*, 29(10:2189-2195 (2006).

Elliott, et al., "Parenteral absorption of insulin from the lung in diabetic children," *Austr. Paediatr. J.* 23: 293-297 (1987).

Engelgau, et al., "Screening for tyoe 2 diabetes," *Diabetes Care* 1563(23):1-31 (2000).

Festa, et al., "LDL particle size in relation to insulin, proinsulin, and insulin sensitivity" *Diabetes Care* 22(10):1688-1693 (1999).

Garber, "Premixed insulin analogues for the treatment of diabetes mellitus", *Drugs*, 66(1):31-49(2006).

Gupta, "Contemporary Approaches in Aerosolized Drug Delivery to the Lung," *J. Controlled Release*, 17(2): 127-147 (1991).

Haffner, et al., "Proinsulin and insulin concentrations I relation to carotid wall thickness" *Stroke* 29:1498-1503 (1998).

Hagedorn, et al., "Protamine insulin", *JAMA*, 106:177-180 (1936).

Hanley et al., "Cross-sectional and prospective associations between proinsulin and cardiovascular disease risk factors in a population experiencing rapid cultural transition" *Diabetes Care* 24(7):1240-1247 (2001).

Heinemann, et al. "Current Status of the development of inhaled insulin" *Br. J. Diabetes Vase Dis* 4:295-301 (2004).

Heubner, et al. Klinische Wochenschrift 16:2342 (1924).

Heyder, "Alveolar deposition of inhaled particles in humans," *Am. Ind. Hyg. Assoc. J.* 43(11): 864-866 (1982).

Heyder, *"Particle Transport onto Human Airway Surfaces" Eur. J. Respir. Dis. Suppl.* 119:29-50 (1982).

Johnson, et al., "Turbuhaler®: a new device for dry powder terbutaline inhalation," *Allergy* 43(5):392-395 (1988).

Jones, et al., "An investigation of the pulmonary absorption of insulin in the rat", *Third European Congress of Biopharmaceutics and Pharmacokinetics*, (1987).

Kang, et al., "Subcutaneous insulin absorption explained by insulin's physiochemical properties", *Diabetes Care*, 14:942-948 (1991).

Karl, et al., Pramlintide as an adjunct to insulin in patients with type 2 diabetes in a clinical practice setting reduced AIC, postprandial glucose excursions, and weight, *Diabetes Technology and Therapeutics*, 9(2):191-199 (2007).

Katchalski, "Synthesis of Lysine Anhydride," *J. Amer. Chem. Soc.*, 68: 879-880 (1946).

Keowmaneechai, et al., "Influence of EDTA and citrate on physiochemical properties of whey protein-stabilized oil-in-water emulsions containing $CaCl_2$", *J. Agricultural and Food, Chemistry*, 50:7145-7153 (2002).

Klauser, et al., "Mixtures of human intermediate and human regular insulin in type 1 diabetic patients", *Diabetes Res. and Clin. Practice*, 5:185-190 (1988).

Kohler, "Aerosols for Systemic Treatment", *Lung Suppl.* 677-683 (1990).

Kohler, et al. "Non-radioactive approach for measuring lung permeability: inhalation of insulin," *Atemw Lungebkrkh* 13:230-232 (1987).

Komada, et al., "Intratracheal delivery of peptide and protein agents: absorption from solution and dry powder by rat lung," *J. Pharm. Sci.* 83(6): 863-867 (1994).

Kontny, et al. "Issues Surrounding MDI Formulation Development with Non-CFC Propellants," *J. Aerosol Med.* 4(3), 181-187 (1991).

Kopple, "A Convenient Synthesis of 2,5-Piperazinediones," *J. Org. Chem.*, 33(2): 862-864 (1968).

Leahy, "Beta-cell dysfunction in type II diabetes mellitus," *Curr. Opin. Endocrinol. Diabetes* 2(4): 300-306 (1995).

Lee, et al., "Development of an Aerosol Dosage Form Containing Insulin", *J. Pharm. Sci.*, 65(4), 567-572 (1976).

Lian, et al., "A self-complementary, self-assembling microsphere system: application for intravenous delivery of the antiepileptic and neuroprotectant compound felbamate," *J Pharm Sci*, 89:867-875 (2000).

Lim, "Microencapsulation of Living Cells and Tissues," *J. Pharm. Sci.*, 70: 351-354 (1981).

Mathiowitz, "Morphology of Polyanhydride Microsphere Delivery Systems," *Scanning Microscopy*, 4: 329-340 (1990).

Mathiowitz, "Novel Microcapsules for Delivery Systems," *Reactive Polymers*, 6: 275-283 (1987).

Mathiowitz, "Polyanhydride Microspheres As Drug Carriers I. Hot-Melt Microencapsulation," *J. Controlled Release*, 5: 13-22 (1987).

Mathiowitz, "Polyanhydride Microspheres As Drug Carriers II. Microencapsulation by Solvent Removal," *J. Applied Poly. Sci.*, 35: 755-774 (1988).

Mathiowitz, "Polyanhydride Microspheres IV. Morpohology and Characterization of Systems Made by Spray Drying," *J. Applied Poly. Sci.*, 45: 125-134 (1992).

Moench & Dehnen, "High-performance liquid chromatography of polypeptides and proteins on a reversed-phase support", *Journal of Chromatography*, 147:415-418 (1978).

Nagai, et al., "Powder Dosage Form of Insulin for Nasal Administration," *J. Control Rel.*, 1:15-22 (1984).

Nilsson, et al., "Low levels of asparagine deamidation can have a dramatic effect on aggregation of amyloidogenic peptides: implications for the study of amyloid formation", *Protein Science*, 11(2): 342-349 (2002).

Okumura, et al., "Intratracheal delivery of insulin. Absorption from solution and aerosol by rat lung," *Int. J. Pharmaceuticals* 88: 63-73 (1992).

Patton & Platz, "Routes of Delivery: Case Studies. Pulmonary delivery of peptides and proteins for systemic action," *Adv. Drug. Del. Rev.* 8: 179-196 (1992).

Pfeiffer, "Insulin secretion in diabetes mellitus," *Am. J. Med.* 70(3): 579-88 (1981).

Pfutzner, et al., "Influence of small dose i.v., s.c. and pulmonary insulin treatment on prandial glucose control in patients with type 2 diabetes" 37th *Annual Meeting of the EASD, Glasgow*, Sep. 9-13, 2001 812 (2001) (abstract).

Polonsky, et al., "Abnormal patterns of insulin secretion in non-insulin-dependent diabetes mellitus," *N. England J. Med.* 318(19): 1231-39 (1988).

Prabhu, et al. "A study of factors controlling dissolution kinetic of zinc complexed protein suspensions in various ionic species", *Int. J. Pharm.*, 217(1-2):71-8 (2001).

Quinn, et al., "Minimizing the aggregation of insulin solutions", *J. Pharmaceutical Sci.*, 72:1472-1473 (1983).

Raskin, et al., "Continuous subcutaneous insulin infusion and multiple daily injection therapy are equally effective in type 2 diabetes" *Diabetes Care* 26:2598-2603 (2003).

Raz, et al. "Pharmacodynamic and pharmacokinetics of dose ranging effects of oralin versus s.c. regular insulin in Type 1 diabetic patients," *Fourth Annual Diabetes Technology Meeting*, Philadelphia, PA, 2004.

Rosenstock, et al., "Reduced hypoglycemia risk with insulin glargine: a meta-analysis comparing insulin glargine with human NPH insulin in type 2 diabetes", Diabetes Care, 28(4):950-5 (2005).

Sakr, "A new approach for insulin delivery via the pulmonary route: design and pharmacokinetics in non-diabetic rabbits", *International Journal of Pharmaceutics*, 86:1-7 (1992).

Salib, "Utilization of Sodium Alginate in Drug Microencapsulation," *Pharazeutische Industrie*, 40(11a): 1230-1234 (1978).

Sawhney, "Bioerodible Hydrogels Based on Photopolymerized Poly-(ethylene glycol)-co-poly(a-hydroxy acid) Diacrylate Macromers," *Macromolecules*, 26: 581-587 (1993).

Schlueter, et al., "Pulmonary Administration of Human Insulin in Volunteers and Type I Diabetics", *Diabetes*, 33 (Suppl.): 298 (1984).

Schneider, et al., "Stimulation by proinsulin of expression of plasminogen activator inhibitor type-I in endothelial cells" *Diabetes* 41(7):890-895 (1992).

Steiner, et al. "Technosphere®/ Insulin- proof of concept study with new insulin formulation for pulmonary delivery" *Exp. Chin. Endocrinol. Diabetes* 110:17-21 (2002).

Szepesy & Horvath, "Specific salt effects in hydrophobic interaction chromatogaphy of proteins", *Chromatographia*, 26:13-18 (1988).

Todo, et al., "Effect of additives on insulin absorption from intracheally administered dry powders in rats", *Int. J. Pharmaceutics*, 220:101-110 (2001).

Warren, et al., "Postprandial versus preprandial dosing of biphasic insulin aspart in elderly type 2 diabetes patients" *Diabetes Research and Clinical Practive* 66:23-29 (2004).

Waterhouse, et al. "Comparative assessment of a new breath-actuated inhaler in patients with reversible airways obstruction" *Respiration* 59:155-158 (1992).

Wigley, et al., "Insulin across respiratory mucosae by aerosol delivery," *Diabetes* 20(8): 552-556 (1971).

Witchert, "Low Molecular Weight PLA: A Suitable Polymer for Pulmonary Administered Microparticles," *J. Microencapsulation*, 10(2): 195-207 (1993).

Yoshida, et al., "Absorption of insulin delivered to rabbit trachea using aerosol dosage form," *J. Pharm. Sci.* 68(5): 670-671 (1979).

Zethelius, et al., "Proinsulin is an Independent Predictor of Coronary Heart Disease" *Circulation* 105:2153-2158 (2002).

U.S. Appl. No. 12/397,219, filed Mar. 3, 2009, Steiner, et al.

Bensch, et al., "Absorption of intact protein molecules across the pulmonary air-tissue barrier," *Science* 156: 1204-1206 (1967).

Culy, et al., "Management of diabetes mellitus: Defining the role of insulin lispro mix 75/25", *Dis. Man. Health. Outcome*, 9(12): 711-730 (2001).

Humalog®, Mix 75/25™ "Patient Information", Eli Lilly, pp. 1-4, accessed Jun. 18, 2009.

Koehler, et al., "Pulmonary Administration," Abstract 298, *Diabetes* 33 (Suppl.):75A (1984).

Lalli, et al., "Long-term intensive treatment of type 1 diabetes with the short-acting insulin analog lispro in variable combination with NPH insulin at mealtime", *Diabetes Care*, 22(3):468-77 (1999).

Molitch, et al., "How long should insulin be used once a vial is started?", *Diabetes Care*, 27(5)1240-1; author reply 1241-2 (2004).

Moren, "Aerosol dosage forms and formulations" in *Aerosols in Medicine*, (2nd ed.), Elsevier, pp. 321-350 (1993).

Plum, et al., "Pharmacokinetics of the rapid-acting insulin analog, insulin aspart, in rats, dogs, and pigs, and pharmacodynamics of insulin aspart in pigs.", *Drug Metab. Dispos.*, 28(2):155-60 (2000).

Roach, et al., "Improved postprandial glycemic control during treatment with Humalog Mix25, a novel protamine-based insulin lispro formulation. Humalog Mix25 Study Group", *Diabetes Care*, 22(8):1258-61 (1999).

* cited by examiner

RAPID ACTING AND LONG ACTING INSULIN COMBINATION FORMULATIONS

CROSS-REFERENCE TO RELATED APPLICATIONS

This application claims priority to U.S. Ser. No. 60/990,814 entitled "Rapid Acting and Long Acting Insulin Combination Formulations" filed Nov. 28, 2007. This application is a continuation-in-part of U.S. Ser. No. 11/695,562 entitled "Rapid Acting and Long Acting Insulin Combination Formulations" filed Apr. 2, 2007, by Solomon S. Steiner and Roderike Pohl, which claims priority to U.S. Ser. No. 60/744,687 entitled "Rapid Acting and Long Acting Insulin Combination Formulations" filed Apr. 12, 2006 by Solomon S. Steiner and Roderike Pohl. This application is also a continuation-in-part of U.S. Ser. No. 11/537,335 entitled "Rapid Acting and Prolonged Acting Insulin Preparations" filed Sep. 29, 2006 by Solomon S. Steiner and Roderike Pohl, which claims priority to U.S. Ser. No. 60/721,698, filed on Sep. 29, 2005.

The disclosures in the applications listed above are herein incorporated by reference.

FIELD OF THE INVENTION

The present invention generally relates to formulations combining rapid acting and long acting insulin formulations.

BACKGROUND OF THE INVENTION

Intensive insulin therapy for diabetes involves providing a basal insulin, ideally present at a uniform level in the blood over a 24 hour period and a bolus or meal time (prandial) insulin to cover the added carbohydrate load from digestion concomitant with each meal.

In 1936, Hans Christian Hagedorn and B. Norman Jensen discovered that the effects of injected insulin could be prolonged by the addition of protamine obtained from the "milt" or semen of river trout. The insulin was added to the protamine and the solution was brought to pH 7 for injection. In 1946, Nordisk Company was able to form crystals of protamine and insulin and marketed it in 1950 as NPH, (Neutral Protamine Hagedorn, "NPH") insulin. NPH insulin has the advantage that it can be mixed with an insulin that has a faster onset to compliment its longer lasting action. Eventually all animal insulins were replaced by human recombinant insulin.

Until very recently, and in many places today, basal insulin is usually provided by the administration of two daily doses of NPH insulin, separated by 12 hours. A patient eating three meals a day and using NPH insulin as the basal insulin requires five injections per day, one with each of three meals and two NPH insulin injections, one in the morning and the other at bedtime. To reduce the number of injections the patient must take, the morning dose of NPH insulin has been combined with a short acting insulin (recombinant human insulin) or a rapid acting insulin analog, such as lispro, A typical combination is a 70% NPH to 30% rapid acting insulin analog mixture. As a result, the patient can reduce the number of injections from five per day to four per day. See, e.g., Garber, *Drugs* 66(1):31-49 (2006).

Insulin glargine, which is currently sold under the trade name LANTUS® (Sanofi-Aventis Deutschland GmbH), is marketed as a "long-acting" insulin analog. LANTUS® can have up to 24 hour duration. LANTUS® typically starts to lower blood glucose about one hour after injection. J. Rosenstock and colleagues found that patients who took insulin glargine had a much lower risk of low blood glucose (hypoglycemia) than the patients who took NPH insulin. While LANTUS® is designed to cover the average patient's basal insulin needs over a 24 hour time period, the reality is that for many patients, it does not last long enough, causing them to be hyperglycemic, typically in the early morning hours. For some patients, LANTUS® is effective for only 12 hours, for others it is effective for 18 hours, and for still others it is effective for 24 hours. In an attempt to make LANTUS® last for 24 hours, the dose of LANTUS® is frequently increased. Unfortunately in these cases the risk of nocturnal hypoglycemia is also increased, which is a serious life-threatening condition that can lead to death.

Glargine cannot be mixed with other short or rapid acting insulins because the mixture causes glargine to precipitate prior to injection and administration of a precipitated insulin makes it virtually impossible to administer a known and reliable dose. The manufacturer of glargine warns users against mixing glargine with any other insulin.

It is therefore an object of the present invention to provide insulin formulations that can be used to reduce the number of daily injections to three.

It is another object of the present invention to provide a basal-bolus insulin formulation.

It is still another object of the present invention to provide a stable insulin formulation having immediate and long term release characteristics.

SUMMARY OF THE INVENTION

A combined fast or rapid acting-long acting insulin formulation has been developed wherein the pH of the fast or rapid acting insulin is adjusted so that both rapid and long acting insulins remain soluble when they are mixed together. Alternatively a very rapid acting insulin that has a pH at which the long acting insulin is soluble may be combined with the long acting insulin. Included in the preferred embodiment are any very rapid, rapid or fast acting insulin formulations combined with any intermediate, long or very long acting insulin at low pH. In another embodiment, any very rapid, rapid, or fast acting insulin can be combined with any intermediate, long or very long acting insulin at low pH, in the presence of a chelating agent and dissolution agent. In the most preferred embodiment, VIAJECT™ (a very rapid acting insulin formulation containing a zinc chelator and dissolution agent) is mixed with insulin glargine at pH 4 to produce a rapid initial spike in blood insulin concentration to cover the carbohydrates being absorbed from digestion of a meal and continue with a sustained release of insulin to produce a basal blood insulin level.

LANTUS® may be mixed with VIAJECT™, allowing a reduction in the number of daily insulin injections from 4 to 3. The compatibility of these formulations is due, in part, to the similarity in pH. When LANTUS® is combined with VIAJECT™, there is a change in the duration and magnitude of the glucose lowering effect of the long acting insulin analog. As disclosed herein, 7 out of 8 patients that have been followed for a 24 hour period of time showed a shorter duration of LANTUS® action when given as a single injection, compared to the identical dose given to the same patient in two separate injections administered at the same time. The duration and magnitude of the effect can also be varied by altering the ratio of the VIAJECT™ to LANTUS®. Thus by manipulating, i.e. shortening, the duration of the LANTUS®-containing formulation to 12 hours, the total number of injections that a patient would be required to take in a day, and achieve intensive glycemic control, can be reduced from 4 to 3 injections/day.

Experiments have been performed to demonstrate the importance of the addition of specific acids such as aspartic acid, glutamic acid, maleic, fumaric, or succinic acid to hexameric insulin to enhance speed and amount of absorption and preserve bioactivity following dissociation into the dimeric/monomeric form of insulin. These are added in addition to a chelator, preferably ethylenediaminetetraacetic acid (EDTA). Acids were selected based on their molecular size and structure to optimize association with hydrogen bonding sites on the insulin surface, effectively masking charged amino acid residues (see FIG. 1). The acids were used at a concentration that provided optimal charge masking effect. As shown by the examples, the preferred acids are aspartic, glutamic, succinic, maleic, fumaric and citric acid. The combination of both the preferred acid and the chelator together in the insulin formulation appear to be responsible for rapid insulin absorption. EDTA was not effective with all acids. When used with adipic acid, oxalic acid or HCl, there was no apparent increase in the rate of absorption of insulin. These studies establish the importance of an acid and chelator in both in vitro (human oral epithelial cells) and in vivo (rat pig and human) studies. These findings confirm the results seen in patients with diabetes treated with the very rapid acting insulin (in combination with citric acid and EDTA) and the basal insulin glargine.

DETAILED DESCRIPTION OF THE INVENTION

I. Definitions

Figure 1:
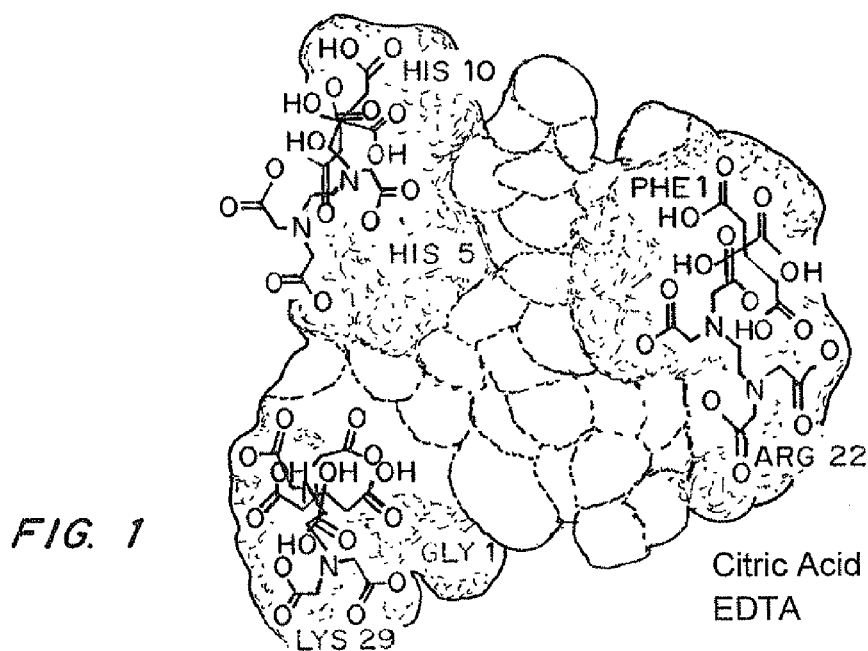
FIG. 1 is a three dimensional schematic of insulin showing charges. Cationic residues on insulin are represented with shading. The citric acid and EDTA molecules are overlayed on the cationic residues.

As used herein, "insulin" refers to human or non-human, recombinant, purified or synthetic insulin or insulin analogues, unless otherwise specified.

As used herein, "human insulin" is the human peptide hormone secreted by the pancreas, whether isolated from a natural source or made by genetically altered microorganisms. As used herein, "non-human insulin" is from an animal source such as pig or cow.

As used herein, an "insulin analogue" is an altered insulin, different from the insulin secreted by the pancreas, but still available to the body for performing the same action as natural insulin. Through genetic engineering of the underlying DNA, the amino acid sequence of insulin can be changed to alter its ADME (absorption, distribution, metabolism, and excretion) characteristics. Examples include insulin lispro, insulin glargine, insulin aspart, insulin glulisine, insulin detemir. The insulin can also be modified chemically, for example, by acetylation. As used herein, human insulin analogues are altered human insulin which is able to perform the same action as human insulin.

As used herein, a "chelator" or "chelating agent" refers to a chemical compound that has the ability to form one or more bonds to zinc ions. The bonds are typically ionic or coordination bonds. The chelator can be an inorganic or an organic compound. A "chelate complex" is a complex in which the metal ion is bound to two or more atoms of the chelating agent.

As used herein, "duration of action" refers to the time period following administration of an insulin-containing formulation to reestablish baseline glucose blood levels (i.e. 120 mg/dl) post nadir.

As used herein "nadir" refers to the lowest glucose blood levels achieved following administration to a patient of an insulin-containing formulation.

As used herein, a "solubilizing agent" is a compound that increases the solubility of materials in a solvent, for example, insulin in an aqueous solution. Examples of solubilizing agents include surfactants (TWEENS®); solvent, such as ethanol; micelle forming compounds, such as oxyethylene monostearate; and pH-modifying agents.

As used herein, a "dissolution agent" is an acid that, when added to insulin and EDTA, enhances the transport and absorption of insulin relative to HCl and EDTA at the same pH, as measured using the epithelial cell transwell plate assay described in the examples below. HCl is not a dissolution agent but may be a solubilizing agent. Citric acid is a dissolution agent when measured in this assay.

As used herein, an "excipient" is an inactive substance other than a chelator or dissolution agent, used as a carrier for the insulin or used to aid the process by which a product is manufactured. In such cases, the active substance is dissolved or mixed with an excipient.

II. Formulations

The formulations are suitable for subcutaneous administration and include insulin, a chelator and a dissolution agent(s) and one or more other excipients, as required, to make a formulation suitable for subcutaneous administration. The formulation will typically contain VIAJECT™ and LANTUS® in a ratio of units of insulin in VIAJECT™: units of insulin in LANTUS® from 1:0.5 to 1:20, preferably ranging from 1:1 to 1:10.7. In a preferred embodiment, the formulation contains a ratio of units of insulin in VIAJECT™: units of insulin in LANTUS® of 1:1. This formulation typically has a duration of action of 12 hours.

By combining the ingredients in VIAJECT™ (citric acid, EDTA and insulin) in different proportions/ratios, in combination with LANTUS®, one can control the magnitude and duration of the glucose lowering effect in patients with diabetes.

The composition includes a fast, rapid or very rapid acting insulin and an intermediate or long acting insulin. The rapid acting insulin is provided at a low pH, at which the long acting insulin does not precipitate when mixed together, even over a wide range of ratios of rapid acting to long acting insulin.

There are several differing types of commercial insulin available for diabetes patients. These types of insulins vary according to (1) how long they take to reach the bloodstream and start reducing blood glucose levels; (2) how long the insulin operates at maximum strength; and (3) how long the insulin continues to have an effect on blood sugar.

Fast Acting Insulin

Fast acting insulins are intended to respond to the glucose derived from ingestion of carbohydrates during a meal. Fast acting insulins start to work within one to 20 minutes, peaking about one hour later and lasting from three to five hours. Fast acting insulin takes about two hours to fully absorb into the systemic circulation. Fast acting insulins include regular recombinant human insulin (such as Humulin®, marketed by Eli Lilly®, and Novalin®, marketed by NovoNordisk®) which are administered in an isotonic solution at pH 7. Bovine and porcine insulins, which differ in several amino acids to human insulin, but are bioactive in humans, are also fast acting insulins.

Rapid Acting Insulin.

Some diabetes patients use rapid-acting insulin at mealtimes, and long-acting insulin for 'background' continuous insulin. This group includes insulins that have been modified or have altered locations of amino acids in order to enhance their rate of absorption.

At present there are three types of rapid-acting commercial insulin analogs available: lispro insulin (Lysine-Proline insulin, sold by Eli Lilly® as HUMALOG®), glulisine insulin (sold by Sanofi-Aventis® as APIDRA®) and aspart insulin (sold by Novo Nordisk® as NOVOLOG®).

Very Rapid acting Insulin

Biodel has a proprietary insulin formulation of regular human insulin that is even more rapid than the rapid acting insulin analogs, VIAJECT™. This is a formulation combining regular human insulin with EDTA and citric acid, at a pH of 4.

Intermediate Acting Insulin

Intermediate-acting insulin has a longer lifespan than short-acting insulin but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedorn) and LENTE® (insulin zinc suspension) insulin. NPH insulin contains protamine which slows down the speed of absorption so that the insulin takes longer to reach the bloodstream but has a longer peak and lifespan. Intermediate acting insulins may be combined with rapid acting insulins at neutral pH, to reduce the total number of injections per day.

Long Acting Insulin

A long acting insulin is insulin glargine is marketed under the tradename LANTUS®. The extended duration of action of LANTUS® is normally induced by the ph elevation from 4 to 7 post subcutaneous injection. This changes the solubility of the insulin glargine, creating a microprecipitate. This microprecipitate slowly dissolves in the subcutaneous tissue, sustaining its glucose lowering effect for up to 24 hours.

LANTUS® (insulin glargine) is a recombinant human insulin analog that can have up to 24 hour duration. It differs from human insulin by having a glycine instead of asparagine at position 21 and two arginines added to the carboxy-terminus of the beta-chain.

LANTUS® consists of insulin glargine dissolved in a clear aqueous fluid. Each milliliter of LANTUS® (insulin glargine injection) contains 100 IU (3.6378 mg) insulin glargine. Inactive ingredients for the 10 mL vial are 30 µg zinc, 2.7 mg m-cresol, 20 mg glycerol 85%, 20 µg polysorbate 20, and water for injection. Inactive ingredients for the 3 mL cartridge are 30 µg zinc, 2.7 mg m-cresol, 20 mg glycerol 85%, and water for injection. The pH is adjusted by addition of aqueous solutions of hydrochloric acid and sodium hydroxide. LANTUS® has a pH of approximately 4 prior to injection.

The median time between injection and the end of the pharmacological effect is a maximum of 24 hours after the injection. The median time between injection and the end of pharmacological effect was 24 hours for insulin glargine and 14.5 hours for NPH human insulin The package insert says not to mix LANTUS® with any other types of insulin, unlike most rapid acting and intermediate acting insulins, due to precipitation of the insulins on mixing.

In the case of insulin glargine, there is no precipitate formed on mixing with VIAJECT™ which also has a pH of 4, matching that of the insulin glargine. Ultimately, this combination provides very rapid acting insulin to carry the patient through a meal with less bolus insulin, since it is very rapidly absorbed and eliminated shortly after meal digestion, thereby reducing the chance of hypoglycemia and providing 24 hour long lasting basal insulin. This ultimately reduces the number of injections required per day from four to three.

The choice of dissolution agent and chelator, the concentration of both the dissolution agent and the chelator, and the pH that the formulation is adjusted to, all have a profound effect on the efficacy of the system. While many combinations have efficacy, the preferred embodiment is chosen for many reasons, including safety, stability, regulatory profile, and performance.

In the preferred embodiment, at least one of the formulation ingredients is selected to mask any charges on the active agent. This may facilitate the transmembrane transport of the insulin and thereby increase both the onset of action and bioavailability for the insulin. The ingredients are also selected to form compositions that dissolve rapidly in aqueous medium. Preferably the insulin is absorbed and transported to the plasma quickly, resulting in a rapid onset of action (preferably beginning within about 5 minutes following administration and peaking at about 15-30 minutes following administration).

The chelator, such as EDTA, chelates the zinc in the insulin, thereby removing the zinc from the insulin solution. This shifts the equilibrium toward the dimeric and monomeric form and retards reassembly into the hexameric state. Since these two forms exist in a concentration-driven equilibrium, as the monomers are absorbed, more monomers are created. Thus, as insulin monomers are absorbed, additional dimers dissemble to form more monomers. The monomeric form has a molecular weight that is less than one-sixth the molecular weight of the hexameric form, thereby markedly increasing both the speed and quantity of insulin absorbed. To the extent that the chelator (such as EDTA) and/or dissolution agent (such as citric acid) hydrogen bond with the insulin, it is believed that it masks the charge on the insulin, facilitating its transmembrane transport and thereby increasing both the onset of action and bioavailability for insulin.

The insulin can be recombinant or purified from a natural source. The insulin can be human or non-human. Human is preferred. In the most preferred embodiment, the insulin is human recombinant insulin. Recombinant human insulin is available from a number of sources. The insulin may also be an insulin analogue which may be based on the amino acid sequence of human insulin but having one or more amino acids differences, or a chemically modified insulin or insulin analog.

The dosages of the insulin depends on its bioavailability and the patient to be treated. The actual systemic dose delivered to an individual ranges from 3 to 100 IU. For insulin with only 2.5% bioavailability, an oral dose of 4000 IU will deliver a 100 IU systemically available dose. For insulin with a much greater bioavailability, such as 50% bioavailability, delivery of a 3 IU systemically available dose requires an oral dose of only 6 IU.

Dissolution Agents

Certain acids appear to mask charges on the insulin, enhancing uptake and transport. Those acids which are effective as dissolution agents include acetic acid, ascorbic acid, citric acid, glutamic, aspartic, succinic, fumaric, maleic, and adipic, relative to hydrochloric acid, as measured in the transwell assay described in the examples below. A preferred dissolution agent is citric acid. Hydrochloric acid may be used for pH adjustment, in combination with any of the formulations, but is not a dissolution agent.

The amount of dissolution agent in the formulation is effective at masking charges on the insulin, and enhancing uptake of the insulin compared to the insulin alone. Preferably the formulation is between $9.37 \times 10^{-4}$ M to $9.37 \times 10^2$ M citric acid.

Chelators

In the preferred embodiment, a zinc chelator is mixed with the insulin. The chelator may be ionic or non-ionic. Suitable chelators include ethylenediaminetetraacetic acid (EDTA), ethylene-bis(oxyethylene nitro) tetraacetic acid (EGTA), di-, tri-sodium citrate, chlorella, cilantro, 1,2-Diaminocyclohexanetetraacetic acid (CDTA), dimercaptosuccinic acid (DMSA). Hydrochloric acid is used in conjunction with TSC to adjust the pH, and in the process gives rise to the formation of citric acid, which is a dissolution agent.

In the preferred embodiment, the chelator is EDTA. It is known that the chelator captures the zinc from insulin, thereby favoring the dimeric form of the insulin over the hexameric form and facilitating absorption of the insulin by the tissues surrounding the site of administration. In addition, the chelator hydrogen may bond to the active agent, thereby aiding the charge masking of the active agent and facilitating transmembrane transport of the active agent.

The amount of the chelator in the formulation is effective to enhance uptake of the insulin compared to the insulin alone.

In the preferred embodiment, the chelator is EDTA. Preferably the formulation is between $2.42 \times 10^{-4}$ M to $9.68 \times 10^{-2}$ M EDTA.

Formulations

The active compounds or pharmaceutically acceptable salts thereof may be administered in the form of a pharmaceutical composition wherein the active compound(s) is in admixture or mixture with one or more pharmaceutically acceptable carriers, excipients or diluents. In a preferred embodiment the insulin is administered by injection, preferably subcutaneously (s.c.). The formulation for injection will typically be suspended in sterile water, phosphate buffered saline, saline or glycerin.

Other suitable pharmaceutically acceptable carriers, excipients or diluents are known. For example, solubilizing agents include wetting agents such as polysorbates and poloxamers, non-ionic and ionic surfactants, food acids and bases (e.g. sodium bicarbonate), and alcohols, and buffering acids or salts for pH control.

Stabilizers are used to inhibit or retard drug decomposition reactions which include, by way of example, oxidative reactions. A number of stabilizers may be used. Suitable stabilizers include polysaccharides, such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphosphatidylserine; phosphatidylglycerols; phosphatidylinositols; cardiolipins; sphingomyelins; and synthetic detergents, such as dioctanoylphosphatidyl choline and polyethylene-polypropylene glycol).

Other pharmaceutically acceptable excipients, solubilizing agents or other agents may be added to the insulin in lyophilized or dried form immediately before use, but may be added prior to use.

III. Methods of Making the Formulations

Pharmaceutical compositions may be formulated in a conventional manner using one or more physiologically acceptable carriers comprising excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Baston, Pa. (1975), and Liberman, H. A. and Lachman, L., Eds., Pharmaceutical Dosage Forms, Marcel Decker, New York, N.Y. (1980). Proper formulation is dependent upon the route of administration chosen.

In the preferred embodiment, the formulation suitable for subcutaneous administration is formed by mixing the clinically desired amount of VIAJECT™ with LANTUS®, in a ratio that is titered to a specific patient's insulin requirements. The clear solutions are mixed and then injected subcutaneously into the patient. Mixing may occur in a separate vessel or within the syringe.

Figure 8:
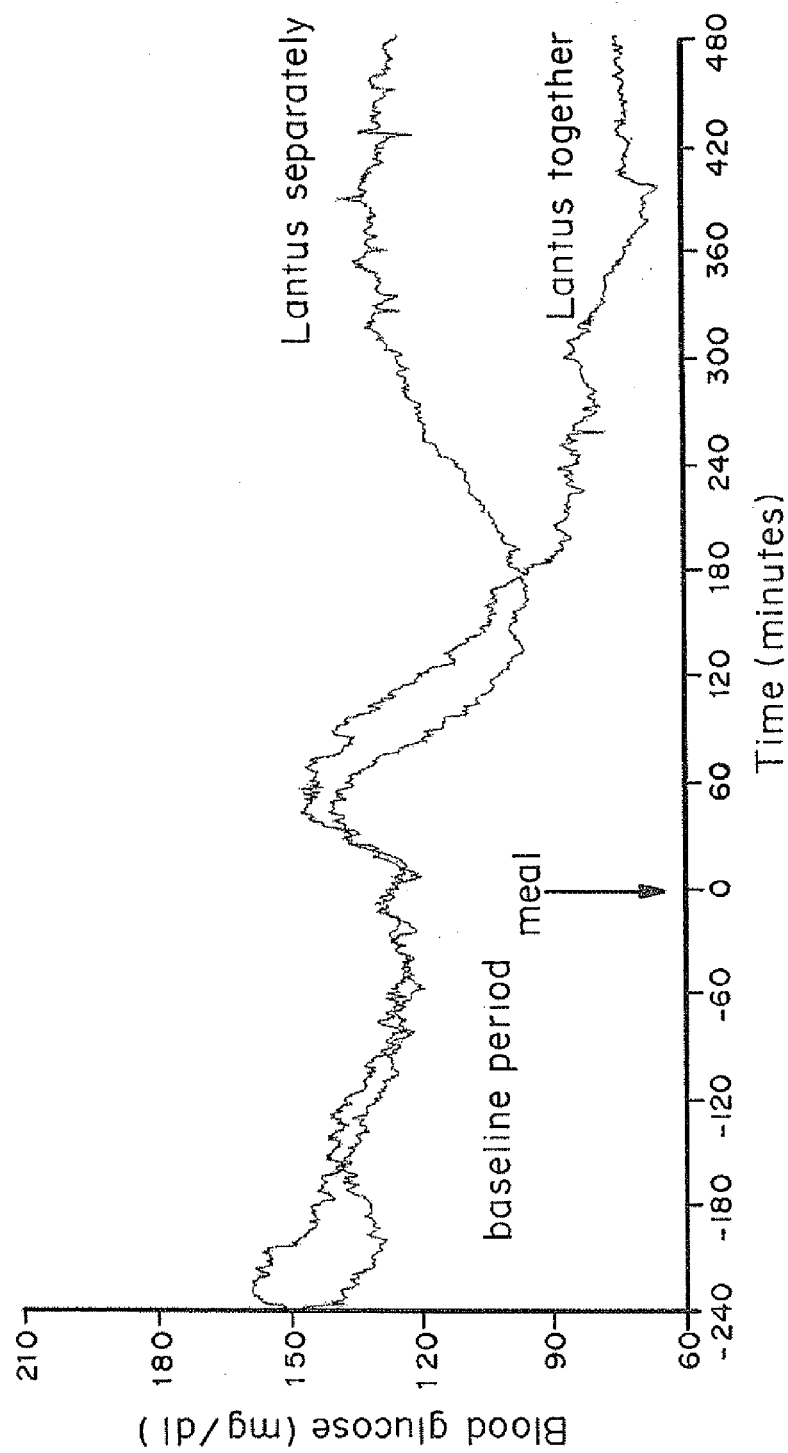
FIG. 8 is a graph of mean continuous blood glucose values (mg/dL) over time (minutes) for a total of 8 hours from a human clinical trial, where insulin glargine (LANTUS®) and VIAJECT were administered separately (two injections) or together, i.e. combined in one injection, for nine patients.
Figure 9:
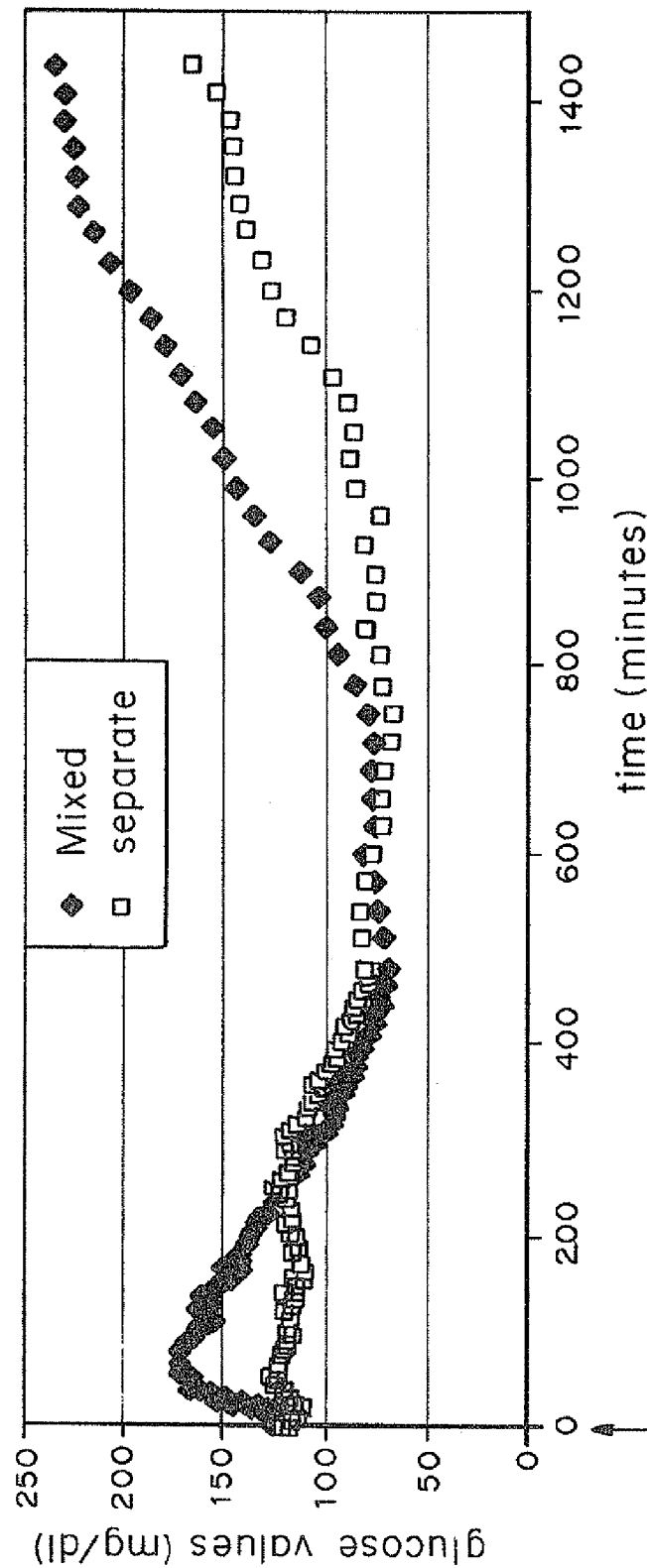
FIG. 9 is a graph of mean continuous blood glucose values (mg/dL) over time (minutes) for 8 hours and mean blood glucose values obtained every 30 minutes for a total of 24 hours from a human clinical trial, where insulin glargine (LANTUS®) and VIAJECT were administered separately (two injections) or together, i.e. combined in one injection, for seven patients.
Figure 10:
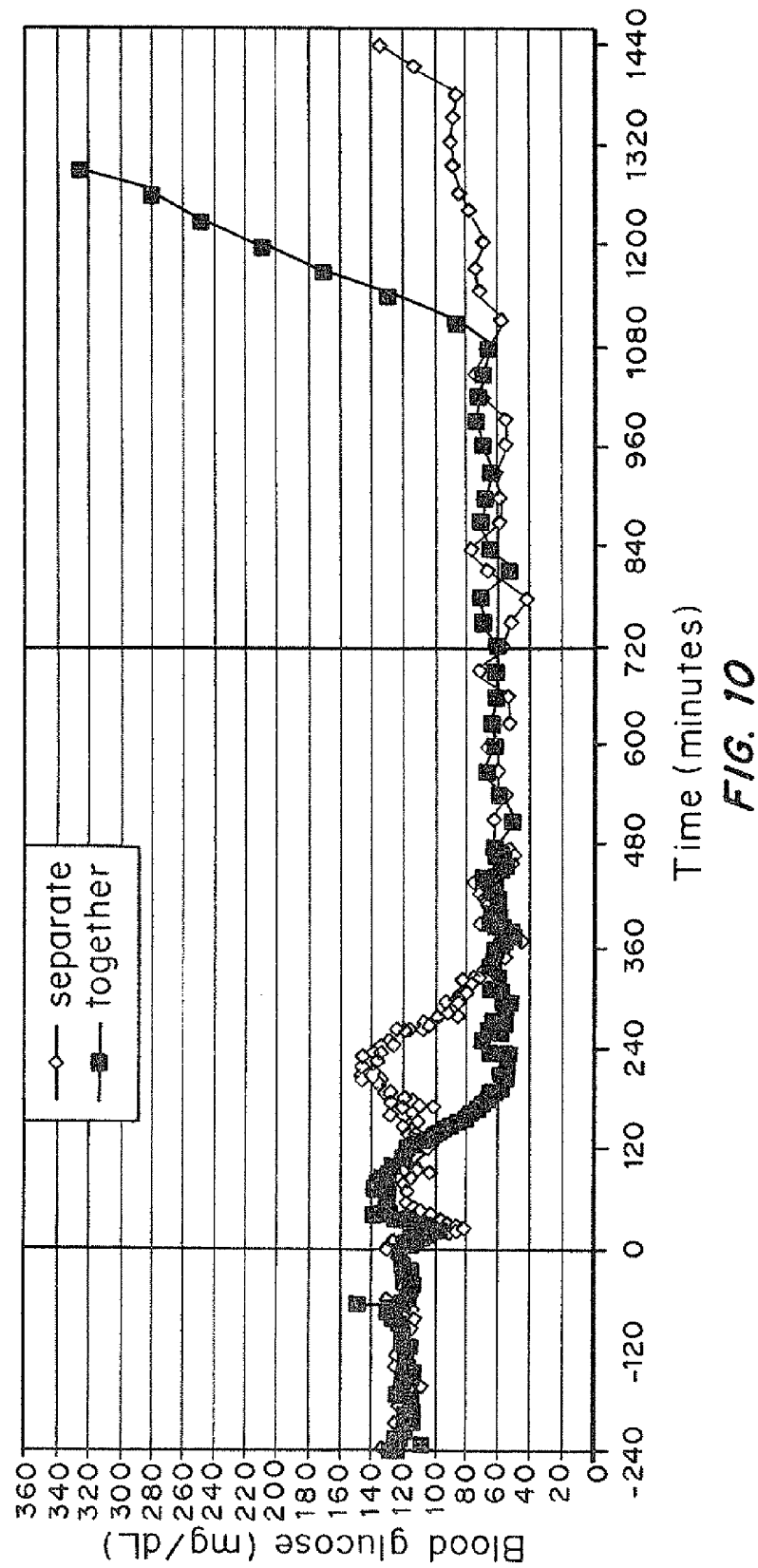
FIG. 10 is a graph of continuous blood glucose values (mg/dL) over time (minutes) from a single patient from a clinical trial where insulin glargine (LANTUS®) and VIAJECT™ were administered separately (two injections) or together, combined in one injection syringe.

FIGS. 8-10 show data on human clinical trials on a subcutaneously injectable mixture of VIAJECT™ and insulin glargine (LANTUS®).

IV. Methods of Using Formulations

Although insulin formulations may be administered in a variety of manners, the formulations described herein are designed from delivery by injection, preferably subcutaneously. Following administration, the dosage form dissolves quickly releasing the drug or forming small particles containing drug, optionally containing one or more excipients. The formulation is designed to be rapidly absorbed and transported to the plasma for systemic delivery.

When LANTUS® is administered together with VIAJECT™, there is a change in the duration and magnitude of the glucose lowering effect of the long acting insulin analog. The duration and magnitude of the effect can also be varied by altering the ratio of the VIAJECT™ to LANTUS®. In one embodiment, the ration of VIAJECT™ to LANTUS® is selected to shorten the duration to 12 hours. This allows the total number of injections that a patient would be required to take in a day, and achieve intensive glycemic control, to be reduced from 4 to 3 injections/day. Thus a diabetic patient could administer an insulin formulation containing a combination of a long acting insulin, such as LANTUS®, and a very rapid acting insulin, such as VIAJECT™ in the morning, such as prior to eating breakfast, and then administer a prandial insulin, such as VIAJECT™, prior to eating lunch, and then administer a an insulin formulation containing a combination of a long acting insulin, such as LANTUS®, and a very rapid acting insulin, such as VIAJECT™ in the evening, such as prior to eating dinner.

The present invention will be further understood by reference to the following non-limiting examples.

EXAMPLE 1

Effect of EDTA on Insulin Absorption Through an Epithelial Cell Multilayer

The purpose of this study was to demonstrate in vitro the effect of EDTA in the presence of citric acid on absorption of insulin through an epithelial cell multilayer.

Materials and Methods

Figure 2:
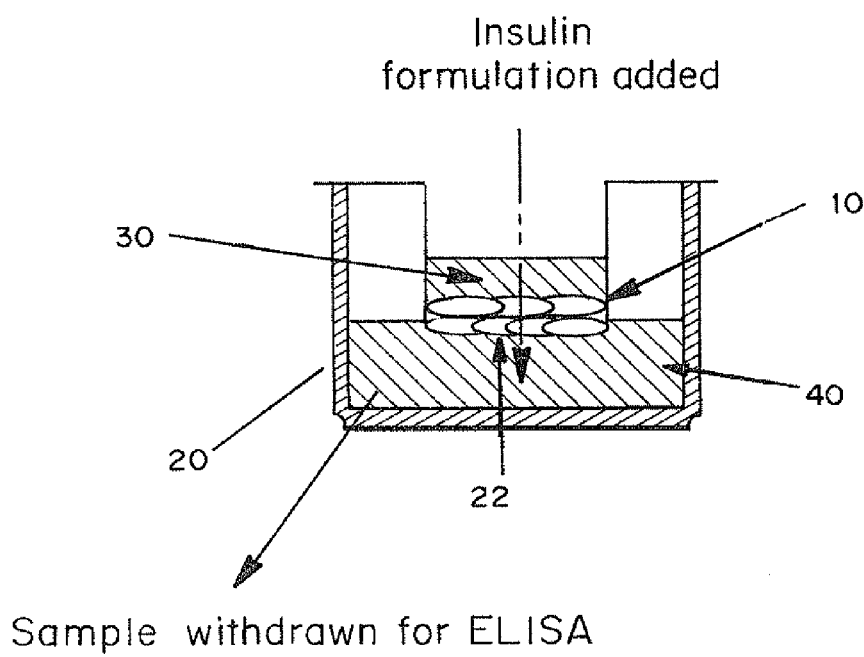
FIG. 2 is a diagram of the transwell device used to measure insulin absorption through oral epithelial cells.

Two saline solutions were mixed. The first contained 1 mg/ml insulin, 2 mg/ml EDTA and 2 mg/ml citric acid ("solution 1"). The second contained 1 mg/ml insulin and 2 mg/ml citric acid ("solution 2"). The control (no cells) contained EDTA, citric acid and insulin. Immortalized human epithelial cell line cultures (10) were seeded on transwell plates (20) FIG. 2. Cells were grown to confluence and tested for membrane integrity using trans-epithelial resistance. A 0.1 µm filter (22) was used. At time zero, the fluid in the top chambers, i.e., donor chamber (30), of the transwell plates was replaced with 0.5 ml of insulin solution, either solution 1 or solution 2-. Two plates with solution 1, two plates with solution 2 and one plate with the control solution (no cells) were tested simultaneously. The lower chamber, i.e., receiver chamber (40), of each plate contained 1.5 mL of saline solution. At each time point, 100 µL of fluid from the lower chamber (40) was removed and analyzed with insulin Enzyme-Linked Immunosorbent Assay (ELISA). 100 µL of saline was added to the lower chamber to maintain a constant volume of 1.5 mL throughout the study.

The amount of insulin removed from the lower chamber at each time point was added to the amount removed in the previous time point(s) to determine the cumulative amount of insulin recovered in the lower chamber. Cells were stained to check for viability before and after the experiment. There was no statistical difference in the cell viability for each of the plates.

Results

Figure 3:
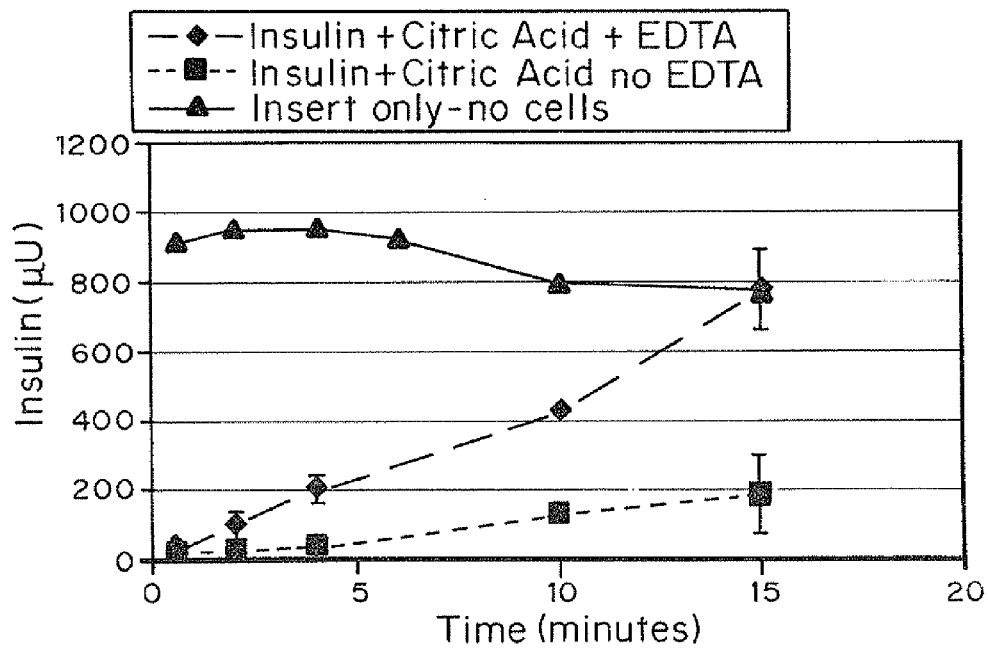
FIG. 3 is a graph of the mean insulin accumulation (µU) over time (minutes) in the Lower chamber of a transwell membrane plate seeded with epithelial cells, comparing the effect of an insulin formulation containing EDTA (♦) with one without EDTA (■), with a control, no cells (▲).

FIG. 3 is a graph of the mean insulin accumulation (µU) over time (minutes) in the lower chamber of a transwell plate seeded with epithelial cells, comparing the effect of an insulin formulation containing EDTA (♦) with one without EDTA (■), with a control, no cells (▲).

Solution 1, which contained EDTA, moved through the multilayer of epithelial cells more effectively than solution 2, which did not contain EDTA. Therefore, the effect of combining EDTA with citric acid is to promote the speed and amount of absorption.

EXAMPLE 2

Effect of Aspartic and Citric Acid on Absorption of Insulin Through an Epithelial Cell Multilayer Methods and Materials Oral epithelial cells that have been seeded on transwell plates were used to determine the rate of absorption through the cell multilayer, as described in example 1. Insulin (1 mg/ml) was dissolved in either aspartic (0.2 mg/mL) or citric acid (2 mg/ml) and EDTA (2 mg/ml) was added to both. Insulin with citric acid (no EDTA) was used as a control. The pH of the solution was approximately 3.5 to 4, and physiological same was present to provide an isotonic environment for the cells (0.85% NaCl, sufficient to produce a range of 280-310 mOsm as measured by freezing point depression, Microsmette, Precision systems, Natick, Mass.). Samples were taken from the receiver chamber and assayed by ELISA (Linco Corp.) for human recombinant insulin (µU/mL).

Results

Figure 4:
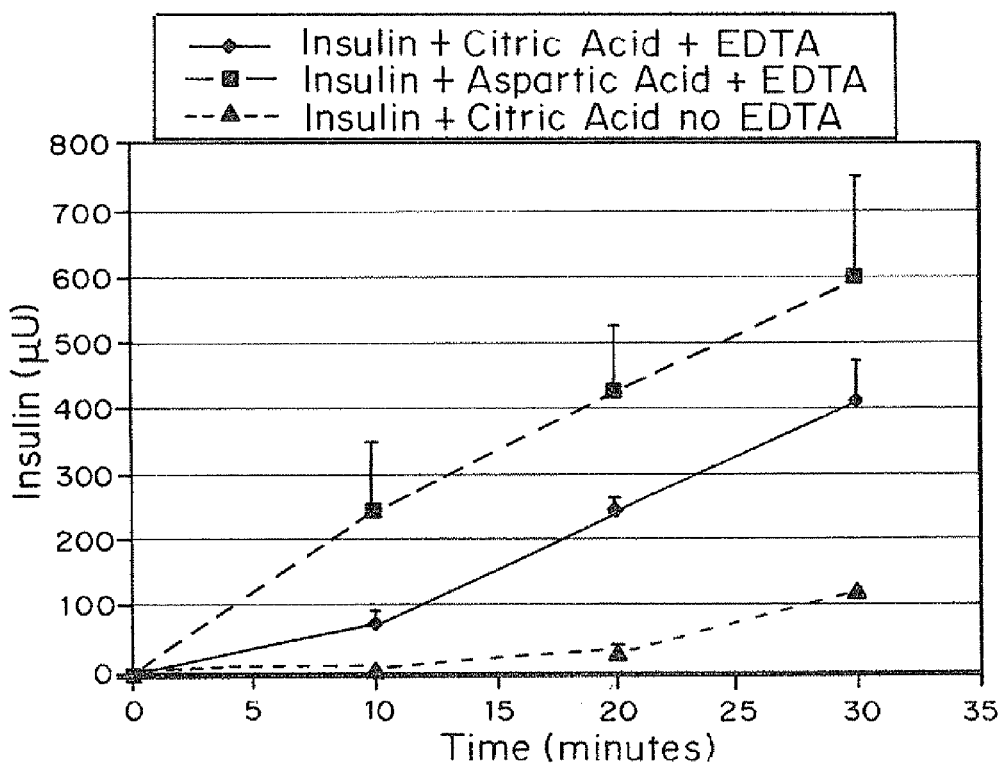
FIG. 4 is a graph of cumulative insulin (µU) over time in minutes for insulin formulations containing citric acid with (♦) and without (▲) EDTA versus insulin formulations containing aspartic acid with EDTA (■).

Insulin/citric acid absorption through the cell layers was enhanced by the addition of EDTA, as shown by Example 2. However, aspartic acid was even more potent at enhancing insulin transport in the presence of EDTA, as shown by FIG. 4.

This study demonstrated that different polyacids in the presence of EDTA have varying effects on insulin absorption, possibly due to varying degrees of charge masking.

EXAMPLE 3

Comparison of Effect of Citric Acid, Glutamic Acid, Adipic Acid and Oxalic Acid on Insulin Absorption Through an Epithelial Cell Multilayer Materials and Methods Transwell plates seeded with oral epithelial cells were used for these experiments. The effect of EDTA was monitored by the amount of insulin that came through the lower chamber of the transwell plate.

Oral epithelial cells were grown on transwell inserts for 2 weeks until multiple (4-5) cell layers had formed. Transport studies were conducted by adding the appropriate solution (all contained 1 mg/ml human insulin) to the donor well and removing samples from the receiver well after 10 minutes. Insulin amounts in the receiver wells were assayed using ELISA. Apparent Permeability was calculated using the formula:

$$\text{Apparent Permeability} = Q/A(C)t$$

where Q=total amount permeated during incubation time in µg, A=area of insert in $cm^2$, C=initial concentration in donor well in $g/cm^3$ and t-total time of experiment in sec.

EDTA concentration is 0.45 mg/mL in all cases and the acid concentrations are as follows: Citric acid 0.57 mg/ml, Glutamic acid 0.74 mg/mL, Adipic acid 0.47 mg/mL, Oxalic acid 0.32 mg/mL. The pH of the solutions was 3.6 in all cases.

Results

Figure 5:
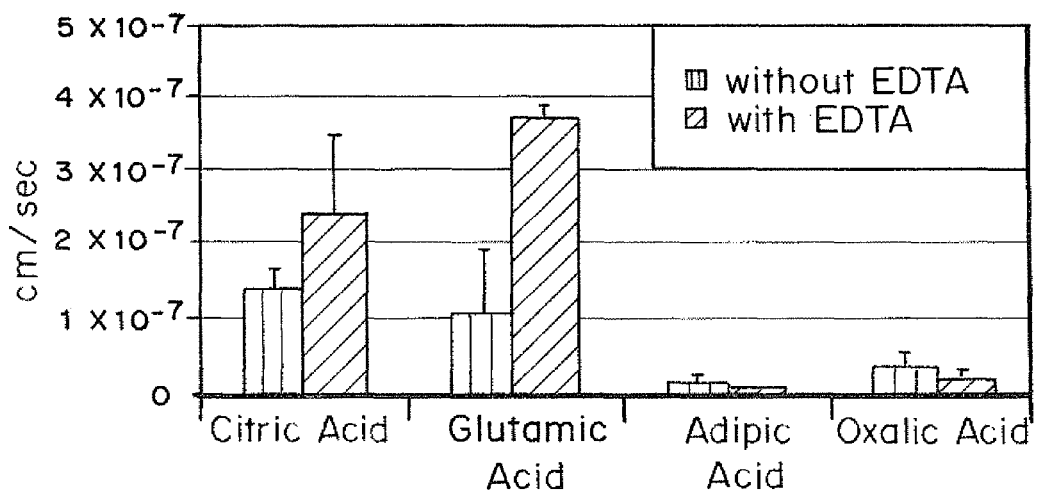
FIG. 5 is a graph of apparent permeability for insulin with (diagonal lines) and without (vertical lines) EDTA, for samples with citric acid, glutamic, adipic, and oxalic acid, over time in minutes.

FIG. 5 shows the change in apparent permeability resulting from different organic polyacids that have been tested, with and without EDTA. The results show that there is an increase in the cumulative amount of insulin apparent permeability when EDTA is added to the acid/insulin in the case of citric and glutamic acids. This did not hold true for all organic polyacids. Adipic and oxalic acids did not show such a response.

EXAMPLE 4

Effect of Acid on Absorption of Insulin from Polymeric Gel Administered Rectally to Rats The purpose of this study was to observe effect of acids and EDTA in an in vivo model.

Materials and Methods

Samples

Insulin was incorporated into a gel consisting of PVA (0.5%), Carbopol (2.7%), CMC (0.005%) and PEG 400 (0.14%), glycerin (0.14%), and EDTA (0.005%) by blending with insulin/aspartic acid or insulin/HCl. The final concentration of insulin in insulin/aspartic acid gel was 0.7 and insulin concentration in insulin/HCl gel was 1.7 mg/g.

Rat Rectal Study

Rats were fasted overnight and were cleared of all fecal matter with a warm water enema. Then the gel formulation was inserted into the rectum and the rat's blood glucose was monitored over an 8 hour time period.

Results

Figure 6:
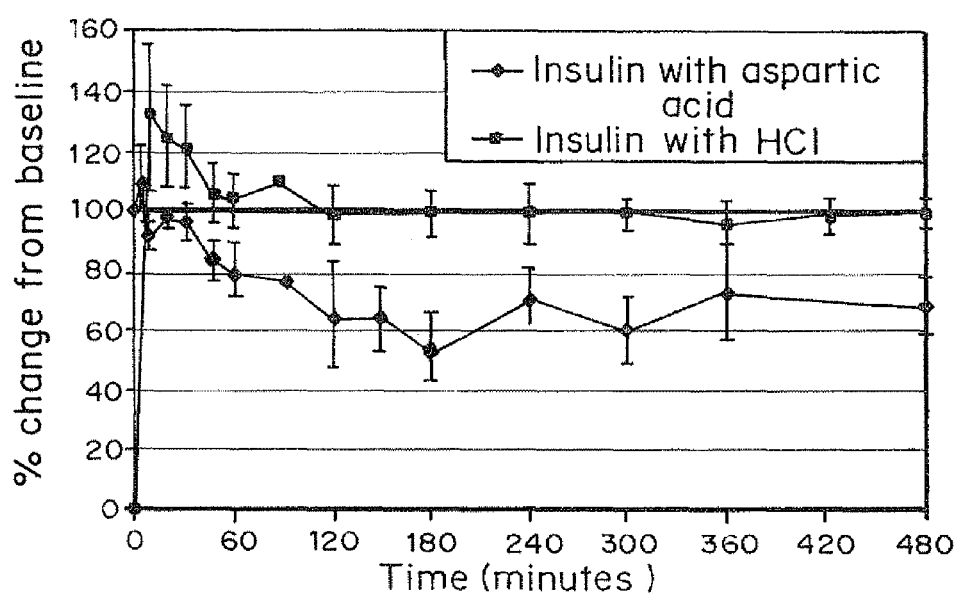
FIG. 6 is a graph of percent glucose lowering from baseline over time in minutes comparing insulin with aspartic acid and EDTA (♦) with insulin with HCl and EDTA (■) in rats.

The results are shown in FIG. 6 as a percent glucose lowering from baseline comparing insulin with aspartic acid and EDTA to insulin with HCl and EDTA. The results show significantly better lowering of glucose for the insulin containing aspartic acid as compared to insulin containing HCl.

EXAMPLE 5

Comparison of Effect of HCl and Citric Acid on Absorption of Insulin with EDTA in Miniature Diabetic Swine The purpose of this study was to look at timing of glucose response when insulin is injected with a polyacid or organic acid in conjunction with EDTA. To further demonstrate that the type of acid is important to the rapid action of the dissociated insulin, a comparison of citric acid to HCl, was performed in miniature diabetic swine.

Materials and Methods

Insulin (0.9 mg/mL) was prepared as a clear isotonic solution containing citric acid (1.8 mg/mL), EDTA (1.8 mg/mL), and m-cresol as a preservative, pH ~4. The comparator was prepared in the same manner, substituting HCl (0.001N) for citric acid and adjusting the pH with NaOH to approximately 4.

Diabetic mini pigs were not fed on the day of the study and were dosed with 0.08 U/kg on three occasions with the HCl formulation. For comparison, the citric acid formulation was used on two occasions with this dose, and four other occasions at a higher dose of 0.125 U/kg. Blood was drawn for insulin and glucose determination over the 8 hour study period.

Results

Figure 7:
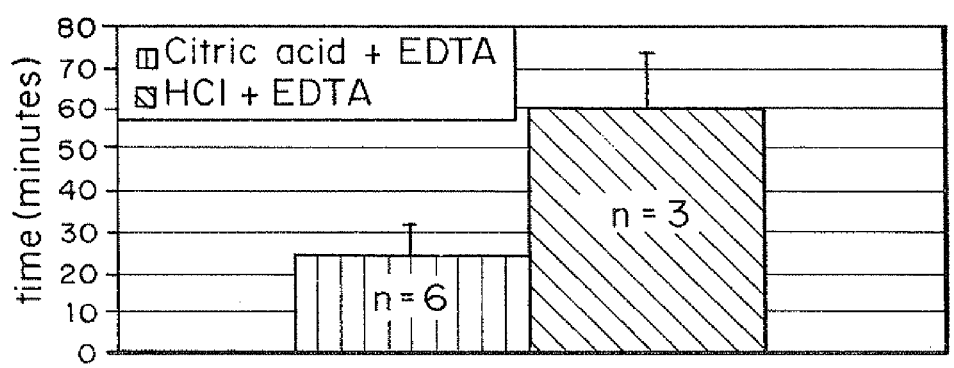
FIG. 7 is a bar graph of mean time to reach the lowest glucose level (nadir) following insulin administration to diabetic mini-pigs, comparing insulin with EDTA and citric acid (vertical lines) versus insulin with EDTA and HCl (diagonal lines).

The results shown in FIG. 7 compare the time to reach the lowest glucose level (nadir) following insulin administration to diabetic mini-pigs. The citric acid formulation was consistently faster at reaching the nadir than an identical formulation made with HCl.

EXAMPLE 6

Insulin Glargine and VIAJECT™ Administered Together and Separately to Patients with Diabetes The purpose of this study was to look at the duration and magnitude of effect on blood glucose when a long acting insulin, LANTUS®, was combined with VIAJECT™.

Methods and Materials

Blood glucose ("BG") of 9 patients (5 males and 4 females; age 40±10 yrs, body mass index ("BMI") 24.0±2.0 kg/m$^2$) were stabilized by glucose clamps (target BG 120 mg/dl). Prior to dosing, the glucose infusion was turned off. Using a cross over design with random treatment order, the same patient specific dose of VIAJECT™ and LANTUS® was injected subcutaneously immediately before the meal. On one occasion, the doses were together in the same injection. On another occasion the identical dose of each insulin was administered separately, at the same time, in two injections. Blood glucose was continuously monitored for 8 hours and glucose infusion was re-initiated if BG was less than 60 mg/dl. Plasma insulin levels were determined throughout the study.

Results

The mean blood glucose data is shown in FIG. 8. The baseline subtracted blood glucose area under the curve ("AUC") following administration of LANTUS® and VIAJECT™, alone or in combination, at 0-60, 0-120, 0-180, 0-480 minutes for the data shown in FIG. 8 were calculated and analyzed. A comparison of the AUC's for a given time period for VIAJECT and LANTUS® administered separately compared to the AUC's for a given time period for VIAJECT™ AND LANTUS® administered together is provided Table 1.

TABLE 1

| VIAJECT ™ and LANTUS ® Together and Separately Before a Standardized Meal Paired T-Test | |
|---|---|
| | p-values |
| AUC 0-60 min | 0.962936 |
| AUC 0-120 min | 0.195853 |
| AUC 0-180 min | 0.264077 |
| Total 0-480 min | 0.000395 |

As shown by the p-values in Table 1, the first three hours have a very similar profile, which is typical of the rapid action of VIAJECT™ after a meal. However, the AUC's for 0-480 are statistically different, indicating a different time-action profile was obtained when LANTUS® and VIAJECT™ were administered together compared when they were administered separately.

An additional nine (9) patients were run over a period of 24 hours. Blood glucose ("BG") of 9 patients were stabilized by glucose clamps (target BG 120 mg/dl). Prior to dosing, the glucose infusion was turned off. Using a cross over design with random treatment order, the same patient specific dose of VIAJECT™ and LANTUS® was injected s.c. immediately before the meal. On one occasion, the doses were together in the same injection. On another occasion the identical dose of each insulin was administered separately (in two injections) at the same time. Blood glucose was continuously monitored for 8 hours and out to 24 hours at 30 minute intervals. Glucose infusion was re-initiated if BG was less than 60 mg/dl. Plasma insulin levels were determined throughout the study. Since two of the patients received incomplete doses during the study, their data was omitted from the data provided below.

The mean blood glucose levels (mg/dl) for seven of these patients are shown in FIG. 9.

The time to reestablish baseline glucose blood levels (120 mg/dl) post nadir, also referred to as "duration of action", was calculated for seven patients and statistically evaluated using a paired t-test. The data is provided for seven patients in Table 2 below.

TABLE 2

Duration of Action of VIAJECT ™ and LANTUS ® administered together or separately

| Patient | Together Duration of action (min) | Separately Duration of action (min) |
|---|---|---|
| A | 960 | 1440 |
| B | 900 | 1260 |
| C | 1170 | 1050 |
| D | 870 | 1440 |
| E | 780 | 930 |
| F | 1140 | 1440 |
| G | 1410 | 1440 | t-Test: Paired Two Sample for Means
P(T <= t) two-tail 0.035019

As shown by the data in Table 2, the duration of LANTUS® is shortened when it is administered together with VIAJECT™, compared to when it is administered separately.

The glucose values for a single patient (Patient F) included in the study described above are shown in FIG. 10. This patient received LANTUS and VIAJECT™ formulations, administered subcutaneously as described above, in a ratio of 1:10.7 (units of insulin in VIAJECT™: units of insulin in LANTUS®). As shown in FIG. 10, even when a patient receives a relatively small amount of VIAJECT™ administered together with LANTUS®, the duration of LANTUS® is shortened compared to when it is administered separately from, but at the same time as, VIAJECT™.

Duration may be further shortened by manipulation of the amount of VIAJECT™ (citric acid, EDTA and insulin) added. VIAJECT™:LANTUS® ratios (based on units of insulin) as low as 1:1.2 and as high as 1:12 were studied. The time to reach the established baseline of 120 mg/dl was determined for seven patients, and the corresponding ratio of VIAJECT™ to LANTUS® is provided in Table 3.

TABLE 3

Effect of ratio of VIAJECT ™ to LANTUS ® on Duration

| Ratio (units of insulin in VIAJECT ™: units of insulin in LANTUS ®) | Time (min) |
|---|---|
| 1:1.2 | 780 |
| 1:1.5 | 840 |
| 1:1.6 | 990 |
| 1:2.1 | 870 |
| 1:2.5 | 900 |
| 1:2.5 | 1200 |
| 1:10.7 | 1140 |

A rank order correlation coefficient was calculated based on the data in Table 3, R=0.875, N=8, p<0.007. There is a statistically significant relationship between the VIAJECT™ to LANTUS® ratio and time to return to baseline (120 mg/dl), demonstrating that increasing the amount of VIAJECT™ (citric acid, EDTA and insulin) reduces the duration of glucose lowering effect seen without these ingredients.

By combining the ingredients in VIAJECT™ (citric acid, EDTA and insulin) in different proportions/ratios, in combination with LANTUS®, one can control the magnitude and duration of the glucose lowering effect in patients with diabetes.

We claim:

1. An injectable formulation comprising a fast acting, rapid acting or very rapid acting insulin including a chelator and a dissolution agent in combination with an intermediate acting in a form suitable for subcutaneous administration.

2. The formulation of claim 1, comprising a very rapid acting insulin.

3. The formulation of claim 1, wherein the chelator is selected from the group consisting of ethylenediaminetetraacetic acid (EDTA), ethylene-bis(oxyethylene nitro) tetraacetic acid (EGTA), trisodium citrate (TSC), alginic acid, alpha lipoic acid, dimercaptosuccinic acid (DMSA), CDTA (1,2-diaminocyclohexanetetraacetic acid).

4. The formulation of claim 3, wherein the chelator is ethylenediaminetetraacetic acid (EDTA).

5. The formulation of claim 1, wherein the dissolution agent is selected from the group consisting of aspartic acid, glutamic acid, maleic, fumaric, succinic and citric acid.

6. The formulation of claim 1, wherein the chelator is EDTA.

7. The formulation of claim 1, wherein the dissolution agent is citric acid.

8. The formulation of claim 1, comprising a very rapid acting insulin and an intermediated acting insulin in a ratio ranging from 1:0.5 to 1:20 (units of insulin in a very rapid acting insulin: units of insulin in an intermediated acting insulin).

9. The formulation of claim 1, comprising a very rapid acting insulin and an intermediated acting insulin in a ratio of 1:1 (units of insulin in a very rapid acting insulin: units of insulin in an intermediate acting insulin).

10. The formulation of claim 1, wherein the very rapid acting insulin is an analog of human insulin suitable for administration to a human.

11. A method of treating a diabetic patient with insulin comprising administering by subcutaneous injection to the patient a formulation comprising a fast acting, rapid acting or very rapid acting insulin including a chelator and a dissolution agent in combination with an intermediate acting insulin.

12. The method of claim 11, wherein the formulation comprises comprising a zinc chelator and a combination of a very rapid acting insulin and an intermediate acting insulin, wherein the dissolution agent is selected from the group consisting of aspartic, glutamic, succinic, maleic, fumaric or citric acid.

13. The method of claim 12, wherein the chelator is EDTA and wherein the dissolution agent is citric acid.

14. The method of claim 13, wherein the formulation has a duration of action of twelve hours following administration to the patient.

15. A method for stabilizing a diabetic patient's blood glucose levels throughout the day comprising administering via subcutaneous injection prior to eating breakfast and prior to eating dinner a formulation comprising an intermediate acting insulin and a very rapid acting insulin, wherein the very rapid acting insulin includes a chelator and a dissolution agent.

16. The method of claim 15, further comprising administering prior to eating lunch a very rapid acting insulin formulation, wherein the formulation comprises a chelator, a dissolution agent and insulin.

* * * * *

UNITED STATES PATENT AND TRADEMARK OFFICE
CERTIFICATE OF CORRECTION

| | | |
|---|---|---|
| PATENT NO. | : 8,084,420 B2 | Page 1 of 1 |
| APPLICATION NO. | : 12/324717 | |
| DATED | : December 27, 2011 | |
| INVENTOR(S) | : Solomon S. Steiner et al. | |

It is certified that error appears in the above-identified patent and that said Letters Patent is hereby corrected as shown below:

Claim 8, column 14, line 27, replace "intermediated" with --intermediate--.
Claim 8, column 14, line 29, replace "intermediated" with --intermediate--.
Claim 9, column 14, line 32, replace "intermediated" with --intermediate--.
Claim 12, column 14, line 44, delete "comprising".

Signed and Sealed this
Fourth Day of December, 2012

David J. Kappos
*Director of the United States Patent and Trademark Office*